(12) United States Patent
Skourlis et al.

(10) Patent No.: US 8,197,674 B2
(45) Date of Patent: Jun. 12, 2012

(54) THIOETHERIFICATION PROCESSES FOR THE REMOVAL OF MERCAPTANS FROM GAS STREAMS

(75) Inventors: Thomas Skourlis, Basking Ridge, NJ (US); Robert J. Gartside, Summit, NJ (US); Robert E. Trubac, Ridgewood, NJ (US)

(73) Assignee: Lummus Technology Inc., Bloomfield, NJ (US)

( * ) Notice: Subject to any disclaimer, the term of this patent is extended or adjusted under 35 U.S.C. 154(b) by 750 days.

(21) Appl. No.: 12/207,390

(22) Filed: Sep. 9, 2008

(65) Prior Publication Data
US 2010/0059413 A1 Mar. 11, 2010

(51) Int. Cl.
*C10G 45/04* (2006.01)
(52) U.S. Cl. ........ 208/246; 208/189; 208/208 R; 208/209; 208/213; 208/217; 62/617; 62/618; 62/620

(58) Field of Classification Search .......... 208/189, 208/208 R, 209, 213, 217, 246; 568/38, 568/57, 60; 62/617–618, 620
See application file for complete search history.

(56) References Cited

U.S. PATENT DOCUMENTS

| | | | |
|---|---|---|---|
| 2,988,500 A | 3/1959 | Gleim et al. | |
| 4,391,677 A * | 7/1983 | Harris et al. | 203/28 |
| 4,626,341 A | 12/1986 | Verachtert | |
| 5,424,051 A | 6/1995 | Nagji et al. | |
| 5,851,383 A | 12/1998 | Frey | |
| 6,231,752 B1 | 5/2001 | Putman | |
| 6,849,773 B2 | 2/2005 | Podrebarac et al. | |
| 6,919,016 B2 | 7/2005 | Podrebarac et al. | |
| 2004/0024272 A1* | 2/2004 | Cheung et al. | 585/261 |
| 2004/0099574 A1* | 5/2004 | Som et al. | 208/210 |
| 2004/0260131 A1* | 12/2004 | Bergmeister et al. | 585/259 |

* cited by examiner

Primary Examiner — Walter D Griffin
Assistant Examiner — Brian McCaig
(74) Attorney, Agent, or Firm — Alix, Yale & Ristas, LLP

(57) ABSTRACT

This invention relates to thioetherification processes for the removal of mercaptans in charge gas streams. In particular, the invention relates to thioetherification processes for the removal of mercaptans using a catalyst comprising palladium and silver.

20 Claims, 3 Drawing Sheets

THIOETHERIFICATION PROCESSES FOR THE REMOVAL OF MERCAPTANS FROM GAS STREAMS

FIELD OF THE INVENTION

The present invention relates to thioetherification processes for the removal of mercaptans in charge gas streams. In one embodiment, the invention relates to thioetherification processes for the removal of mercaptans using a catalyst comprising palladium and silver.

BACKGROUND

Thermal cracking of petroleum-related materials produces a variety of organic chemical components, including mercaptans. One of the products of the thermal cracking process is a gaseous stream, typically referred to as a "charge gas stream", containing various $C_1$ to $C_6$ hydrocarbons, hydrogen and $CO_2$. The hydrocarbon portion of the charge gas stream contains a mixture of olefins, diolefins and acetylenic components. The charge gas stream also typically contains various sulfur containing byproducts of the cracking process, including $H_2S$ and various mercaptans, such as methyl, ethyl, propyl and butyl mercaptans.

The charge gas stream resulting from thermal cracking may contain concentrations of up to 1000 ppm mercaptans. Mercaptans are known to poison or deactivate noble metal selective hydrogenation catalysts. The presence of mercaptans can reduce the effectiveness and life of catalytic hydrogenation reactors, essential parts of conventional charge gas purification and separation processes. Existing caustic scrubber technology of charge gas streams, effective for removal of $H_2S$ and $CO_2$, is ineffective for the removal of mercaptans.

Most industrial processes can tolerate mercaptan concentrations of up to 1000 ppm. Olefin selective hydrogenation systems are designated as either "front-end" (upstream of hydrogen removal) or "back-end" (downstream of hydrogen removal). In conventional back-end or front-end ethylene plants, the mercaptans are separated from the charge gas by distillation before they reach the hydrogenation stage. In back-end systems, due to the boiling point of mercaptans, the mercaptans are contained within the $C_5$+ stream and therefore end up in the pygas stabilization section away from the hydrogenation catalyst. In the first stage of the pygas purification section, liquid phase hydrogenation is performed using a high Pd (<0.4%) or a Ni-based sulphur tolerant catalyst. In the second stage of the pygas purification process, gas phase hydrodesulphurization (HDS) is performed using Co—Mo or Ni—Mo catalysts specifically designed to reduce total sulphur to very low levels.

In one type of front-end system, where the overhead of a depropanizer is fed into a front-end hydrogenation reactor, only methyl-mercaptan is light enough to have an effect. Because the concentration of methyl-mercaptan is normally in the low ppm level at that point, it is expected to have some effect, but this effect can be minimized by the use of higher catalyst loading or higher operating temperatures. The rest of the mercaptans and other sulphur compounds are eliminated in the pygas stabilization section as previously described.

Some industrial processes cannot tolerate mercaptan concentrations of up to 1000 ppm. These processes, such as the front-end CD-Hydro and olefin metathesis reactions, require very low levels of mercaptans in the feed. In the front-end CD-Hydro process, hydrogenation takes place together with distillation before the heavier mercaptans have been removed. The CD-Hydro catalyst, which is a noble metal catalyst, can therefore be deactivated unless mercaptans have been removed from the feed. As a result, it is preferred that mercaptan levels in the feed are at concentrations less than 5 ppm. A traditional solution used commercially to remove oxygenates and sulphur compounds from hydrocarbon streams is an absorber guard bed made of a zeolite material. This is not a viable alternative for these processes because the high reactivity of the charge gas feed will foul the bed, rapidly making it ineffective.

The olefin metathesis process also has very stringent requirements for the mercaptan levels in the feed. Based on their boiling point, certain mercaptans, such as methyl and ethyl-mercaptan, are contained in the $C_4$ olefin stream that feeds the metathesis reactor. Currently, an adsorber bed with a zeolite molecular sieve material is used to remove oxygenates and sulphur compounds from this stream. However, mercaptans can potentially lower the effectiveness of these guard beds to oxygenate removal. Removing the mercaptan compounds upstream from this process in the charge gas treatment area will reduce the absorbent volume requirement and increase the effectiveness of this guard bed in oxygenate removal.

The extraction of mercaptans from hydrocarbon streams is widely practiced in refining. One commercially known process, MEROX®, is described in U.S. Pat. Nos. 2,988,500, 4,626,341 and 5,424,051, each of which is hereby incorporated by reference in its entirety. MEROX®, as well as the related Thiolex process, uses caustic regeneration and has been used in fuel gases, cracked gasoline, LPG streams and heavier fractions. These streams are mostly liquid and have a relatively low olefinic and diolefinic content (i.e., they are not very reactive). Charge gas, on the other hand, has a very high olefinic content with a significant amount of diolefins and acetylenics making these scrubbing methods ineffective.

Thioetherification has been used for the removal of mercaptans from refinery streams. For instance, U.S. Pat. No. 6,231,752 (the entirety of which is hereby incorporated by reference), describes the removal of mercaptans from a light naphtha stream as part of a Catalytic Distillation Hydrosulfurization process using a Ni-based catalyst. This process takes advantage of the thioetherification reaction for sulphur removal via formation of heavy sulphur species components and their removal through the bottoms of the catalytic distillation column. However, the liquid phase reaction mechanism for this technology is only effective for diolefins. In particular, butadiene and isoprene can react with mercaptans to produce thioethers such as butyl-ethyl or $C_5$-ethyl sulfide. U.S. Pat. Nos. 6,849,773 and 6,919,016 (the entirety of each of which is hereby incorporated by reference) describe the same process for a $C_4$ stream.

U.S. Pat. No. 5,851,383 (the entirety of which is hereby incorporated by reference) describes a diolefin hydrogenation-thioetherification process over a Ni-based catalyst on a $C_3$-$C_5$ FCC stream. A combination of a fixed bed hydrogenation reactor and a distillation column are disclosed for the removal of heavy sulphur components. This system is a back end system in which hydrogen is fed as a separate stream, at a low level, with the $C_3$-$C_5$ stream in a fixed bed reactor. The feed stream used in the system described in U.S. Pat. No. 5,851,383 is much lower in reactive species than charge gas.

As such, there exists an ongoing and unmet need in the industry for processes to remove mercaptans from charge gas streams.

SUMMARY OF THE INVENTION

The present invention relates to processes for removing mercaptans from charge gas streams. In one aspect, the invention relates to a process comprising the steps of feeding a gas phase mixture comprising hydrogen, hydrocarbons and mercaptans, which is rich in reactive species such as diolefins and acetylenics, to a reactor comprising a catalyst which is capable of catalyzing the thioetherification of mercaptans to thioethers to produce a reactor product mixture; feeding the reactor product mixture to a distillation unit comprising an upper section and a lower section which is capable of separating lower boiling point hydrocarbons from the thioethers wherein the lower boiling point hydrocarbons are substantially contained in the upper section and the thioethers are substantially contained in the lower section; and recovering the lower boiling point hydrocarbons from the upper section.

In another aspect, the invention relates to a process for removing mercaptans comprising the steps of feeding a gas phase comprising hydrocarbons and mercaptans to a distillation unit comprising (i) a first catalyst which is capable of catalyzing the thioetherification of mercaptans to thioethers, (ii) a gas phase mixture feed point, and (iii) an upper section and a lower section. The distillation unit is capable of separating lower boiling point hydrocarbons from the thioethers. The lower boiling point hydrocarbons are substantially contained in the upper section and the thioethers are substantially contained in the lower section. The feed point is positioned between the first catalyst and the lower section and the lower boiling point hydrocarbons are recovered from the upper section.

In yet another aspect, the present invention relates to a process for removing mercaptans comprising the steps of feeding a liquefied petroleum gas mixture comprising hydrocarbons and mercaptans to a reactor comprising a catalyst which is capable of catalyzing the thioetherification of mercaptans to thioethers to produce a reactor product mixture, wherein the reactor is supplemented with hydrogen gas; feeding the reactor product mixture to a distillation unit comprising an upper section and a lower section which is capable of separating lower boiling point hydrocarbons from the thioethers, wherein the lower boiling point hydrocarbons are substantially contained in the upper section and the thioethers are substantially contained in the lower section; and recovering the lower boiling point hydrocarbons from the upper section.

One advantage of the present invention is that mercaptans present in charge gas streams, including liquefied petroleum gas, at relatively high levels, such as about 1000 ppm, are reduced to relatively lower levels, such as about less than 5 ppm. The mercaptan reduction essentially eliminates the poisoning effect of these mercaptans on sulphur sensitive processes and materials, such as the CD-Hydro catalyst and metathesis catalyst, making both more efficient and economical. Another advantage of the present invention is the reduction of light mercaptans, such as the reduction of methyl-mercaptan in front-end acetylene converter reactors when used between the front-end depropanizer and the hydrogenation reactor. Light mercaptan reduction improves the life and performance of these front-end acetylene converter reactors. These advantages are given by way of non-limiting examples only, and additional benefits and advantages will be readily apparent to those skilled in the art in view of the description set forth herein.

DETAILED DESCRIPTION OF THE INVENTION

The present invention relates to thioetherification processes for the removal of mercaptans in charge gas streams. Conventional caustic scrubber systems and adsorption techniques used to remove sulphur from charge gas streams have very low mercaptan removal capability. The present invention provides for improved sulphur removal from these streams.

The present invention differs from conventional systems and techniques in at least the following way. The present invention uses reactions between components already in the charge gas to remove sulphur. The thioetherification reaction removes mercaptans from the charge gas stream by converting them to less volatile compounds which may then be readily separated from the charge gas stream by fractional distillation. In particular, the reaction joins the mercaptan to olefins, diolefins, and/or acetylenics contained in the charge gas and produces higher molecular weight thioethers. This results in the reactor product mixture comprising high boiling point thioethers.

Thioetherification has been used for the removal of mercaptans from refinery streams in the past. The present invention differs from the prior art thioetherification processes in at least the following ways. The present invention can effectively remove mercaptans from feed gas compositions that comprise significantly higher olefinic and diolefinic content and wider molecular weight ranges, such as hydrogen gas and $C_1$ to $C_6$ hydrocarbons that cannot effectively be removed by prior art processes. The present invention also uses a catalyst comprising palladium and silver as opposed to Ni-based catalysts used in the prior art processes.

In one embodiment, the present invention involves a process comprising the steps of (a) feeding to a reactor a gas phase mixture comprising hydrocarbons and mercaptans to produce a reactor product mixture, wherein said reactor comprises a catalyst which is capable of catalyzing the thioetherification of mercaptans to thioethers; (b) feeding the reactor product mixture to a distillation unit comprising an upper section and a lower section; (c) separating lower boiling point hydrocarbons from the thioethers wherein the lower boiling point hydrocarbons are substantially contained in the upper section and the thioethers are substantially contained in the lower section; and (d) recovering the lower boiling point hydrocarbons from the upper section.

Figure 1:
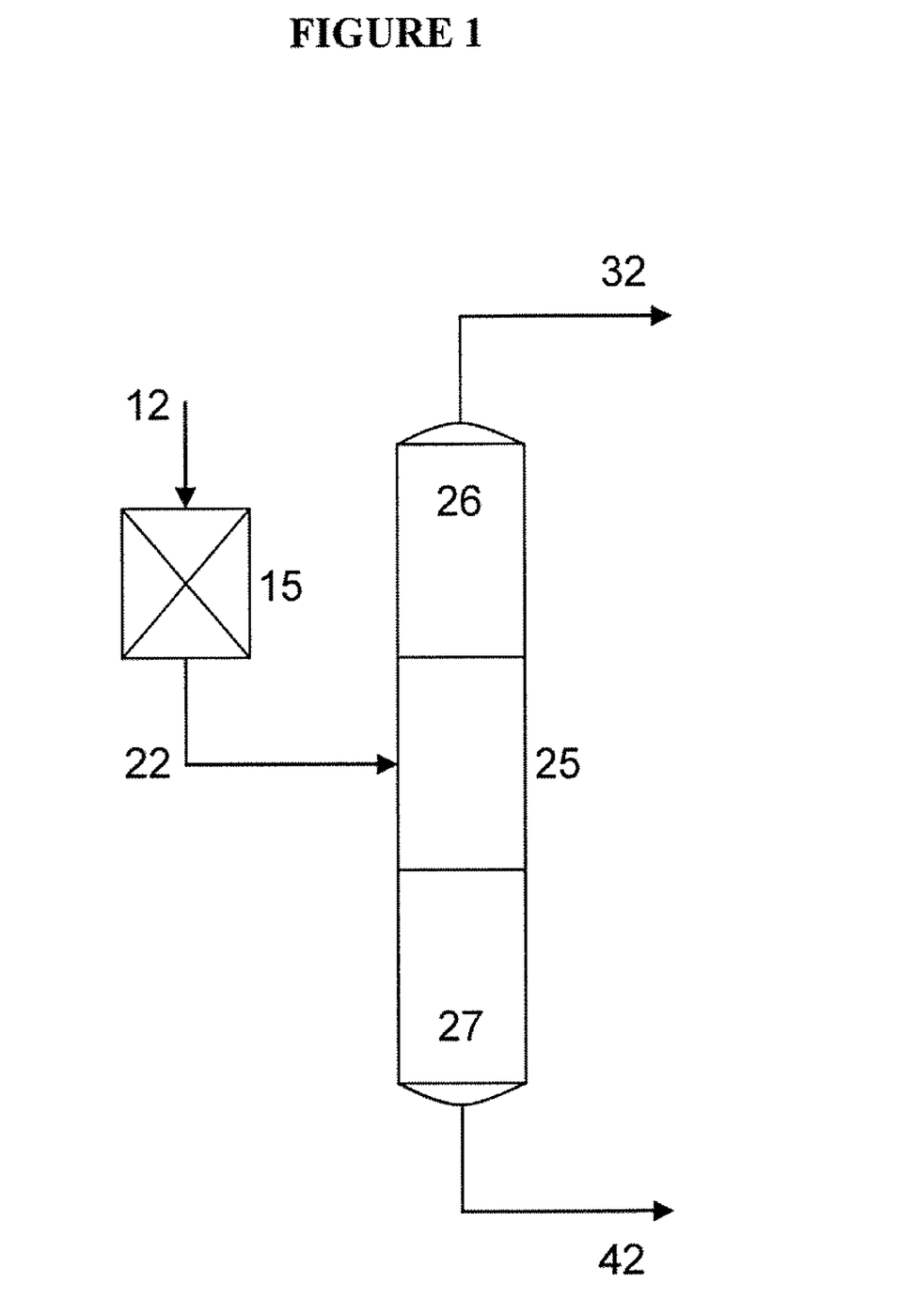
FIG. 1 is a schematic flow chart illustrating an embodiment of the present invention for the removal of mercaptans by thioetherification.

FIG. 1 is a schematic flow chart illustrating one embodiment of the process of the present invention for the removal of mercaptans by thioetherification. The feed, such as a charge gas stream, is fed (12) into the thioetherification reactor (15). The feed may comprise hydrogen gas, hydrocarbons, mercaptans and mixtures thereof. The hydrocarbons typically range from $C_1$ to $C_6$. The hydrocarbons may also comprise olefins, diolefins, acetylenic compounds and mixtures thereof. The mercaptans typically comprise light mercaptans, such as methyl-mercaptan, ethyl-mercaptan, propyl-mercaptans and butyl-mercaptans. Sulphur species such as $H_2S$ may also be present.

The mercaptans may be present in the charge gas stream at concentrations greater than about 5 ppm. Typically, the amount of mercaptans present in the charge gas stream is greater than about 10 ppm, and more typically mercaptans are present in the charge gas stream at concentrations of greater than about 50 ppm. The mercaptan concentration may be as high as 1000 ppm or more in the charge gas stream.

The reactor (15) comprises a catalyst, such as a fixed bed catalyst. The preferred catalyst of the present invention comprises palladium and silver. Preferably, the amount of palladium present in the catalyst is greater than about 100 ppm. More preferably, the amount of palladium present in the catalyst is greater than about 200 ppm. Most preferably, the amount of palladium present in the catalyst is greater than about 500 ppm. Preferably, the amount of silver present in the catalyst is greater than about 50 ppm. More preferably, the amount of silver present in the catalyst is greater than about 100 ppm. The preferred molar ratio of palladium to silver in the catalyst of the present invention ranges from about 0.1 to about 10. More preferably, the molar ratio of palladium to silver in the catalyst of the present invention ranges from about 0.2 to about 1. Most preferably, the molar ratio of palladium to silver in the catalyst of the present invention ranges from about 0.2 to about 0.5.

The reactor (15) is preferably operated at pressures, temperatures and in an atmosphere capable of catalyzing the thioetherification of mercaptans to thioethers. The reactor (15) may also be operated at pressures, temperatures and in an atmosphere capable of hydrogenation of unsaturated hydrocarbons, such as diolefins and acetylenics. In a preferred embodiment, the reactor is operated at a pressure of between about 100 psig and 250 psig, at a temperature of about 120° F. to 250° F.

The reactor product mixture is fed (22) to a distillation unit (25) comprising an upper section (26) and a lower section (27). The reactor product mixture is distilled such that the lighter hydrocarbons are recovered in the overhead (32) and the remaining compounds, including thioethers, exit in the bottoms (42). Preferably, the distillation unit is operated at a pressure of between about 100 psig and 250 psig, at a temperature of about 100° F. to 250° F. Preferably, the overhead stream (32) has a mercaptan concentration of less than about 5 ppm. The overhead stream may have a mercaptan concentration of less than about 2 ppm, and in some embodiments the mercaptan concentration may be less than about 1 ppm.

In an alternative embodiment, the present invention involves a process for removing mercaptans comprising the steps of (a) feeding to a distillation unit a gas phase comprising hydrocarbons and mercaptans, wherein said distillation unit comprises a first catalyst which is capable of catalyzing the thioetherification of mercaptans to thioethers, an upper section, a lower section, and a gas phase mixture feed point, wherein the feed point is positioned between the first catalyst and the lower section; (b) separating lower boiling point hydrocarbons from the thioethers wherein the lower boiling point hydrocarbons are substantially contained in the upper section and the thioethers are substantially contained in the lower section; and (c) recovering the lower boiling point hydrocarbons from the upper section.

Figure 2:
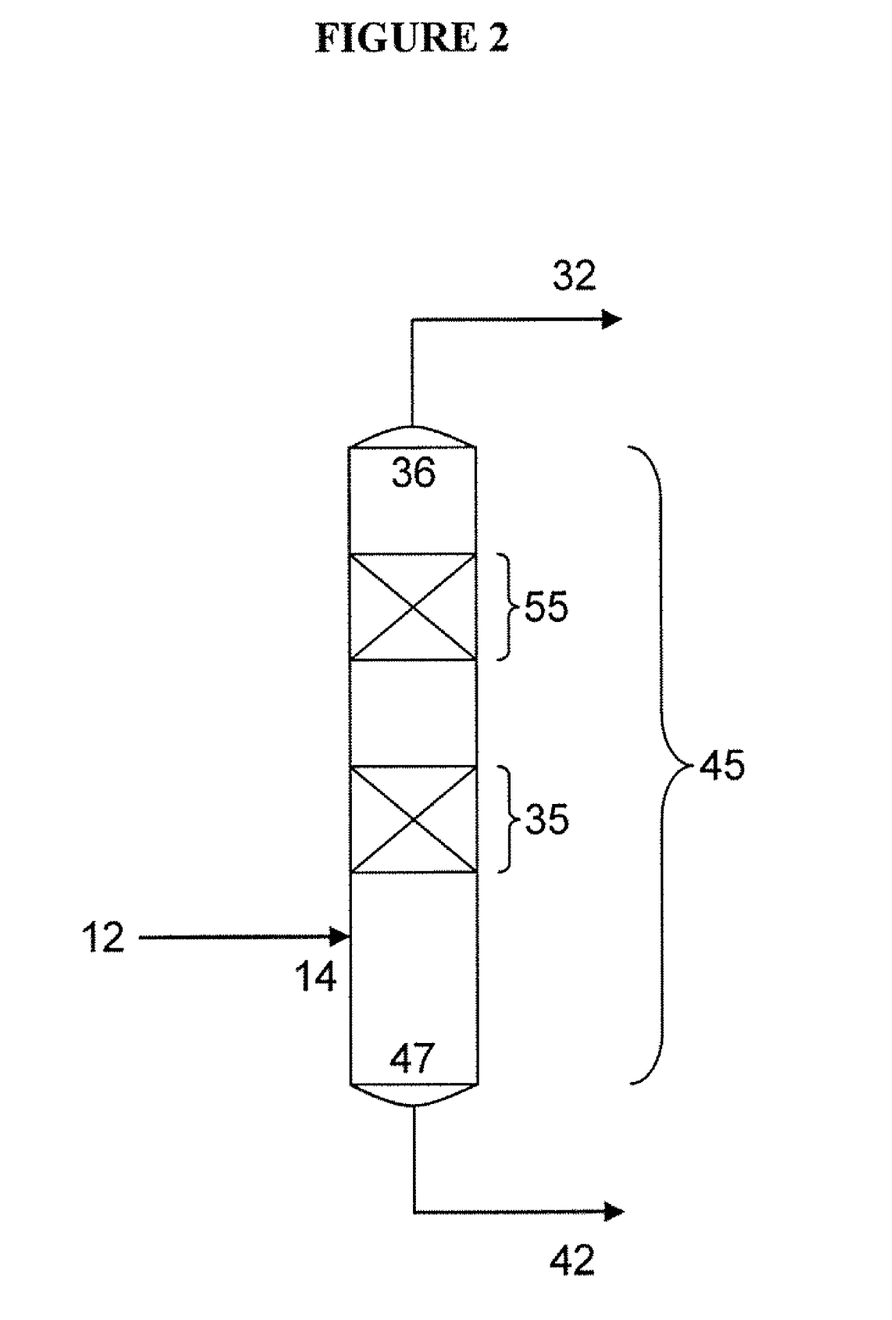
FIG. 2 is a schematic flow chart illustrating an embodiment of the present invention for the removal of mercaptans by thioetherification wherein a first catalyst is used in the form of distillation packing as a lower bed in a catalytic distillation reactor.

FIG. 2 is a schematic flow chart illustrating this alternative embodiment of the process of the present invention wherein a first catalyst is used in the form of distillation packing as a lower bed in a catalytic distillation reactor. The feed, such as a charge gas stream (12), is fed into a catalytic distillation tower (45) at a feed point (14). The feed may comprise hydrogen gas, hydrocarbons, mercaptans and mixtures thereof as previously described. The catalytic distillation tower (45) comprises a thioetherification section (35) and, optionally, a second catalyst section (55). The feed point (14) is positioned between the thioetherification section (35) and the lower section (47) of the distillation tower. The thioetherification section preferably comprises a Pd/Ag catalyst of the type previously described.

The optional second catalyst section (55) is preferably positioned between the thioetherification section (35) and the upper section (36). The second catalyst may be any desired catalyst to promote further reaction of the hydrocarbon components contained in the feed stream to obtain the desired products. The positioning of the thioetherification section (35) above the feed point (14) may be used to guard the optional second catalyst section (55) located higher in the tower (45) from fouling and deactivation from the mercaptans. Because the mercaptans will react over the thioetherification section (35) to form heavier thioethers, the mercaptans will not act as a catalyst poison to the sections located higher in the tower.

In yet another embodiment, the present invention involves a process for removing mercaptans comprising the steps of (a) feeding to a reactor a liquefied petroleum gas mixture comprising hydrocarbons and mercaptans, wherein said reactor comprises a catalyst which is capable of catalyzing the thioetherification of mercaptans to thioethers; (b) supplementing the reactor with hydrogen gas to produce a reactor product mixture; (c) feeding the reactor product mixture to a distillation unit comprising an upper section and a lower section; (d) separating lower boiling point hydrocarbons from the thioethers wherein the lower boiling point hydrocarbons are substantially contained in the upper section and the thioethers are substantially contained in the lower section; and (e) recovering the lower boiling point hydrocarbons from the upper section.

Figure 3:
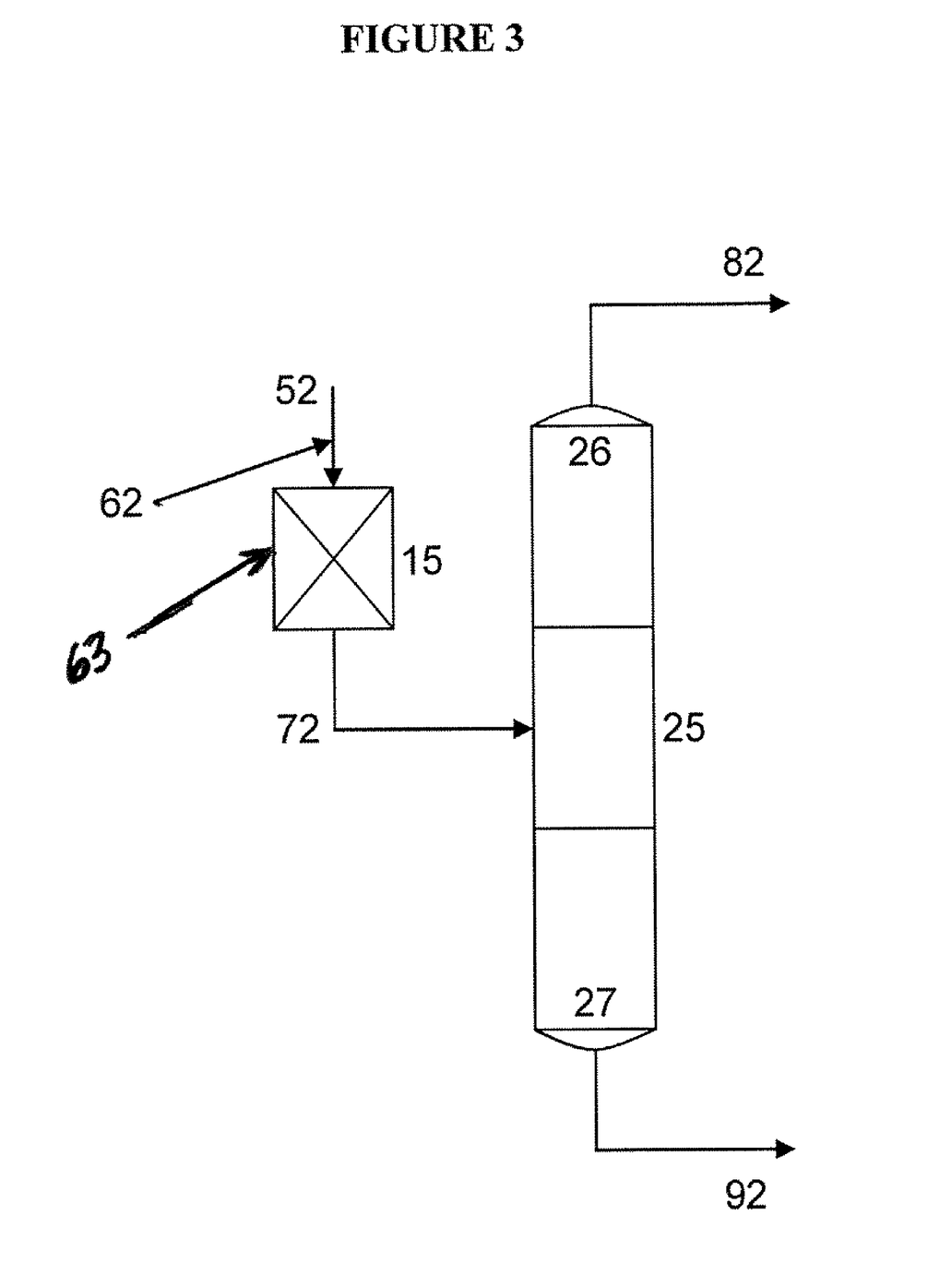
FIG. 3 is a schematic flow chart illustrating an embodiment of the present invention for the removal of mercaptans from liquefied petroleum gas feed by thioetherification.

FIG. 3 is a schematic flow chart illustrating this embodiment of the process of the present invention for the removal of mercaptans from liquefied petroleum gas by thioetherification. The feed (52), such as a liquefied petroleum gas, is fed into the thioetherification reactor (15). The feed (52) may comprise hydrogen gas, hydrocarbons, mercaptans and mixtures thereof as described previously. In a preferred embodiment, the feed is a back-end $C_3$-$C_5$ LPG. The thioetherification reactor preferably contains a Pd/Ag catalyst of the type previously described.

In this embodiment, the thioetherification reactor (15) is supplemented with hydrogen gas. The hydrogen gas may be supplemented in the reactor by addition of hydrogen gas (62) into the feed (52), by addition of hydrogen gas (63) directly to the thioetherification reactor (15), or by addition to both the feed and the reactor. Preferably, the molar ratio of hydrogen gas to the feed ranges from about 0.001 to about 0.5. More preferably, the molar ratio of hydrogen gas to the feed ranges from about 0.01 to about 0.2, and most preferably, the ratio of the amount of hydrogen gas to the amount of feed ranges from about 0.01 to about 0.1.

The reactor (15) is preferably operated at pressures, temperatures and in an atmosphere capable of catalyzing the thioetherification of mercaptans to thioethers. The reactor (15) may also be operated at pressures, temperatures and in an atmosphere capable of hydrogenation of unsaturated hydrocarbons, such as diolefins and acetylenics. In a preferred embodiment, the thioetherification reactor is operated at a pressure of between about 100 psig and 150 psig, at a temperature of about 120° F. to 250° F.

The reactor product mixture is fed (72) to a distillation unit (25) comprising an upper section (26) and a lower section (27). The reactor product mixture is distilled such that the lighter hydrocarbons are recovered in the overhead (82) and the remaining compounds, including thioethers, exit in the bottoms (92). Preferably, the distillation unit is operated at a pressure of between about 100 psig and 250 psig, at a temperature of about 120° F. to 250° F. The tower is typically operated as a dehexanizer (i.e. pentane and lighter components in the overhead stream), which allows the $C_4$ and $C_5$ dienes and the mercaptans to pass through the catalyst zone and the thioethers (which are $C_6+$ fractions) are removed with the bottoms. Preferably, the recovered overhead compounds contains a mercaptan concentration of less than about 5 ppm. The overhead stream may have a mercaptan concentration of less than about 2 ppm, and in some embodiments the mercaptan concentration may be less than about 1 ppm.

One skilled in the art will recognize that numerous variations or changes may be made to the process described above without departing from the scope of the present invention. Accordingly, the foregoing description of preferred embodiments and following examples are intended to describe the invention in an exemplary, rather than a limiting, sense.

Applicants specifically incorporate the entire content of all cited references in this disclosure. Further, when an amount, concentration, or other value or parameter is given as either a range, preferred range, or a list of upper preferable values and lower preferable values, this is to be understood as specifically disclosing all ranges formed from any pair of any upper range limit or preferred value and any lower range limit or preferred value, regardless of whether ranges are separately disclosed. Where a range of numerical values is recited herein, unless otherwise stated, the range is intended to include the endpoints thereof, and all integers and fractions within the range. It is not intended that the scope of the invention be limited to the specific values recited when defining a range.

EXAMPLES

Example 1

A gas phase mixture of hydrocarbons and hydrogen was passed over a fixed bed of hydrogenation catalyst at total pressure of 150 psig. The molar composition of the feed is given in Table 1.

TABLE 1

| Component | Volume (%) |
|---|---|
| Hydrogen | 18.200 |
| Nitrogen | 26.230 |
| Carbon Monoxide | 0.060 |
| Ethyl-Mercaptan | 0.002 |
| Ethylene | 28.554 |
| Acetylene | 0.073 |
| Propane | 0.217 |
| Propylene | 17.832 |
| n-Butane | 0.037 |
| Propadiene | 0.281 |
| T-2-Butene | 0.724 |
| 1-Butene | 5.889 |
| C-2-Butene | 0.228 |
| 1,3-Butadiene | 0.929 |
| Methylacetylene | 0.399 |
| Isoprene | 0.311 |

Gas samples of the feed and product were collected at specified time intervals, in sample bags and analyzed for hydrogen, hydrocarbons and sulphur compounds. An RGA GC was used to test for hydrogen and a FID GC for hydrocarbons. The effluent streams from the laboratory adsorption unit were also analyzed by gas chromatograph equipped with a sulphur chemiluminescence detector (SCD GC). Identification of select components in some samples was achieved by analyzing those samples by GC-MS.

A low Pd (140 ppmw)—low Ag (380 ppmw) catalyst formulation was used. The test was run at 176° F. and gas hourly space velocity (GHSV) of 3,800 $h^{-1}$. The presence of only 20 ppm of mercaptan in the feed had a significant impact on the catalyst activity. At 176° F. the productivity achieved with ethyl mercaptan in the feed was initially 35% of the productivity with the sulphur free feed. After only 24 hrs of testing, a significant drop to less than 10% of its original activity was observed as a result of ethyl mercaptan deactivation. Results are summarized in Table 2 below.

Example 2

A high Pd catalyst was used with 0.4% (i.e. 4,000 ppm) Pd and no Ag. This is a commercial catalyst designated as G68-C by Sud Chemie. This test was done 176° F. and a GHSV of 12,000 $h^{-1}$ with 20 ppm of ethyl-mercaptan. The test had to be run at a much higher space velocity since it is a much more reactive catalyst and the exotherm had to be controlled. The result of this test after 30 hrs was only a slightly (10%) lower productivity with the sulphur compared to the productivity we had achieved with the sulphur free feed. This should be contrasted to the behavior of the catalyst in Example 1, which had showed a very significant drop (65% loss in productivity) immediately after exposure to the ethyl mercaptan feed.

Continued exposure of the G68-C catalyst to this feed was maintained in order to identify any longer term deactivation effects. After completing 120 hours of testing, the drop in catalyst hydrogen productivity was less than 20%. Butadiene conversion had only dropped from 95 to 90% and acetylene conversion from 99 to 97%. The deactivation became much faster between 120 and 150 hrs with $H_2$ productivity dropping to about 10% of the original value. The catalyst deactivation rate was much slower (150 hrs) than the Example 1 catalyst (24 hrs). No unknown sulphur compounds were detected in the product using SCD GC analysis. The results are summarized in Table 2 below.

Example 3

The catalyst used in this example comprised 800 ppm of Pd and 1000 ppm of Ag. The catalyst was tested for its effect on 20 ppmv ethyl-mercaptan at 176° F. and a GHSV of 3,800 $h^{-1}$. In contrast to the low sulphur tolerance of the Example 1 catalyst (which was essentially completely inactive after 30 hrs of testing), the Example 3 catalyst exhibited good acetylene hydrogenation activity even after 70 hrs of testing (60% acetylene conversion from 100% for the fresh catalyst). The butadiene and isoprene conversions were around 5%, down from 90% for the fresh catalyst. And, the MA conversion was 20% down from 90% for the fresh catalyst.

Even further along the test, after 200 hrs, this catalyst still had good acetylene hydrogenation activity. Acetylene conversion stabilized at about 90% (from 100% for the S-free performance) and butadiene and isoprene conversions were around 20% (down from 90% for the sulphur (S)-free performance). Results are summarized in Table 2 below.

TABLE 2

| | | Example 1 | Example 2 | Example 3 |
|---|---|---|---|---|
| S-Free | GHSV | 3800 | 12000 | 3800 |
| | $H_2$ Productivity (lbmoles/lb cat/hr) | 0.005 | 0.07 | 0.008 |

TABLE 2-continued

| | | Example 1 | Example 2 | Example 3 |
|---|---|---|---|---|
| | Acetylene Conversion (%) | 100 | 100 | 100 |
| | Ethylene Gain/Loss (%) | −4 | −34 | −8 |
| | BD Conversion (%) | 95 | 98 | 99 |
| S-Feed SOR | $H_2$ Productivity (lbmoles/lb cat/hr) | 0.0017 | 0.05 | 0.005 |
| | Acetylene Conversion (%) | 97 | 98 | 100 |
| | Ethylene Gain/Loss (%) | 0 | −25 | −1 |
| | BD Conversion (%) | 40 | 95 | 97 |
| S-Feed EOR | $H_2$ Productivity (lbmoles/lb cat/hr) | 0.0002 | 0.003 | 0.003 |
| | Acetylene Conversion (%) | 12 | 34 | 90 |
| | Ethylene Gain/Loss (%) | 0.1 | 0.0 | 0 |
| | BD Conversion (%) | 1 | 17 | 40 |
| | Run Duration (hrs) | 24 | 150 | 230 |

The sulphur analysis of the product showed there was a shift in the sulphur product distribution from ethyl-mercaptan to heavier sulphur species which was quantitative. Identification of the unknown heavier sulphur peaks, about 4 or 5 peaks, in the $C_4$-$C_6$ region in the product was performed. Using GC-MS, the unknown compounds were identified as $C_4$ and C) thioethers both straight chain and cyclic. The most abundant product was diethyl-sulfide followed by ethyl-propyl-sulfide and methyl-tetra-hydro-thiopene. These products are a result of $C_2$ or $C_3$ olefins or diolefins reaction with ethyl-mercaptan through a thioetherification reaction.

The components and their distribution are provided in Table 3.

TABLE 3

| Component | Concentration ppmv | Structure |
|---|---|---|
| 2-methylthietane | 1.8 | |
| Di-ethyl-sulfide | 6.0 | $CH_3-CH_2-S-CH_2-CH_3$ |
| Ethyl-isopropyl sulfide | 2.2 | $CH_3-CH_2-S-CH_2-CH_2-CH_3$ |
| Ethyl-n-propyl sulfide | 2.4 | $CH_3-CH_2-S-CH-(CH_3)_2$ |
| Methyl tetra-hydro-thiophenes | 5.0 | |
| Diethyl-disulfide | 2.0 | $CH_3-CH_2-S-S-CH_2-CH_3$ |
| Total | 19.4 | |

The most abundant product was diethyl-sulfide followed by ethyl-propyl-sulfides and methyl-tetra-hydro-thiophene. These products are potentially a result of unsaturated $C_2$ or $C_3$ compounds with ethyl-mercaptan through a thioetherification reaction. The presence of diethyl-sulfide in particular is an indication that a $C_2$ hydrocarbon either acetylene or ethylene, very much in abundance in the feed, are contributing to the reaction with the mercaptan. Based on these results a combination of Ag and Pd can catalyze these reactions, preferably when both metals are present in sufficiently high enough concentrations (>about 800 ppm).

What is claimed is:

1. A process comprising: (a) feeding to a reactor a gas phase mixture comprising $C_2$-$C_4$ hydrocarbons and 20-1000 ppm mercaptans, wherein the reactor comprises a catalyst which is capable of catalyzing the thioetherification of mercaptans to thioethers by reacting mercaptans with $C_2$ hydrocarbons and $C_3$ hydrocarbons in a gas phase at a pressure in the range of 100 psig to 250 psig, producing a reactor product mixture, the catalyst containing greater than 200 ppm of palladium, and a molar ratio of palladium to silver in the range of 0.1 to 10; (b) feeding the reactor product mixture to a distillation unit comprising an upper section and a lower section; (c) separating lower boiling point hydrocarbons from the thioethers wherein the lower boiling point hydrocarbons are substantially contained in the upper section and the thioethers are substantially contained in the lower section; and (d) recovering the lower boiling point hydrocarbons from the upper section in an overhead stream containing less than 5 ppm mercaptans.

2. The process of claim 1, wherein the catalyst comprises greater than 50 ppm by weight silver.

3. The process of claim 2, wherein the molar ratio of palladium to silver is between 0.2 to 0.5.

4. The process of claim 1, wherein the catalyst comprises greater than 500 ppm by weight palladium and greater than 100 ppm by weight silver.

5. The process of claim 1, wherein the reactor is operated at a pressure of between 100 psig to 250 psig and a temperature of 120° F. to 250° F.

6. The process of claim 1, wherein the catalyzing metals in the catalyst consist essentially of palladium and silver.

7. A process comprising the steps of: (a) feeding to a distillation unit a gas phase comprising $C_2$-$C_4$ hydrocarbons and 20-1000 ppm mercaptans, wherein the distillation unit comprises (i) a first catalyst which is capable of catalyzing the thioetherification of mercaptans to thioethers by reacting mercaptans with $C_2$ hydrocarbons and $C_3$ hydrocarbons in a gas phase at a pressure in the range of 100 psig to 250 psig, the catalyst containing greater than 200 ppm of palladium, and a molar ratio of palladium to silver in the range of 0.1 to 10; (ii) an upper section; (iii) a lower section, and (iv) a gas phase mixture feed point, wherein the feed point is positioned between the first catalyst and the lower section, (b) separating lower boiling point hydrocarbons from the thioethers wherein the lower boiling point hydrocarbons are substantially contained in the upper section and the thioethers are substantially contained in the lower section; and (c) recovering the lower boiling point hydrocarbons from the upper section in an overhead stream containing less than 5ppm mercaptans.

8. The process of claim 7, wherein the catalyst comprises greater than 50 ppm by weight silver.

9. The process of claim 8, wherein the molar ratio of palladium to silver is between 0.2 to 0.5.

10. The process of claim 8 wherein the distillation column further comprises a second catalyst wherein the second catalyst is positioned between the first catalyst and the upper section.

11. The process of claim 7, wherein the catalyst comprises greater than 500 ppm by weight palladium and greater than 100 ppm by weight silver.

12. The process of claim 7, wherein the reactor is operated at a pressure of between 100 psig to 250 psig and a temperature of 120° F. to 250° F.

13. The process of claim 7, wherein the catalyzing metals in the catalyst consist essentially of palladium and silver.

14. A process comprising: (a) feeding to a reactor hydrogen gas and a gas mixture comprising $C_2$-$C_4$ hydrocarbons and 20-1000 ppm mercaptans to produce a reactor product mixture, wherein the reactor comprises a catalyst which is capable of catalyzing the thioetherification of mercaptans to thioethers by reacting mercaptans with $C_2$ hydrocarbons and $C_3$ hydrocarbons in a gas phase at a pressure in the range of 100 psig to 250 psig, the catalyst containing greater than 200 ppm of palladium, and a molar ratio of palladium to silver in the range of 0.1 to 10; (b) feeding the reactor product mixture to a distillation unit, wherein the distillation unit comprises an upper section and a lower section; (c) separating lower boiling point hydrocarbons from the thioethers wherein the lower boiling point hydrocarbons are substantially contained in the upper section and the thioethers are substantially contained in the lower section; and (d) recovering the lower boiling point hydrocarbons from the upper section in an overhead stream containing less than 5 ppm mercaptans.

15. The process of claim 14, wherein the catalyst comprises greater than 50 ppm by weight silver.

16. The process of claim 6, wherein the molar ratio of palladium to silver is between 0.2 to 0.5.

17. The process of claim 14, wherein the catalyst comprises greater than 500 ppm by weight palladium and greater than 100 ppm by weight silver.

18. The process of claim 14, wherein the reactor is operated at a pressure of between 100 psig to 250 psig and a temperature of 120° F. to 250° F.

19. The process of claim 14 wherein the hydrogen gas is mixed with the liquefied petroleum gas mixture prior to being fed to the reactor.

20. The process of claim 14, wherein the catalyzing metals in the catalyst consist essentially of palladium and silver.

* * * * *

UNITED STATES PATENT AND TRADEMARK OFFICE
CERTIFICATE OF CORRECTION

PATENT NO.       : 8,197,674 B2
APPLICATION NO.  : 12/207390
DATED            : June 12, 2012
INVENTOR(S)      : Thomas Skourlis et al.

It is certified that error appears in the above-identified patent and that said Letters Patent is hereby corrected as shown below:

Claim 7, column 10, line 28, delete "$C_2 - c_4$" and insert --$C_2 - C_4$--.

Claim 7, column 10, line 44, delete "5ppm" and insert --5 ppm--.

Claim 16, column 11, line 14, delete "claim 6" and insert --claim 15--.

Signed and Sealed this
Twenty-sixth Day of February, 2013

Teresa Stanek Rea
*Acting Director of the United States Patent and Trademark Office*